United States Patent [19] [11] 4,026,778
Lalonde et al. [45] May 31, 1977

[54] PHOTOCHEMICAL ISOMERIZATION OF VITAMIN A COMPOUNDS

[75] Inventors: Michel Lalonde, Basel; Hansjörg Stoller, Reinach, both of Switzerland

[73] Assignee: Hoffmann-La Roche Inc., Nutley, N.J.

[22] Filed: Nov. 3, 1975

[21] Appl. No.: 628,280

[30] Foreign Application Priority Data

Nov. 12, 1974 Switzerland .................... 15087/74

[52] U.S. Cl. .............................................. 204/159
[51] Int. Cl.² ............................................ B01J 1/10

[58] Field of Search ................................... 204/159

[56] References Cited

UNITED STATES PATENTS 3,838,029  9/1974  Fischer et al. ..................... 204/159

*Primary Examiner*—Howard S. Williams
*Attorney, Agent, or Firm*—Samuel L. Welt; Bernard S. Leon; Richard A. Gaither

[57] ABSTRACT

A novel procedure for photochemical isomerization of vitamin A compounds or derivatives thereof in the absence of sensitizers is disclosed.

6 Claims, No Drawings

PHOTOCHEMICAL ISOMERIZATION OF VITAMIN A COMPOUNDS

BACKGROUND OF THE INVENTION

In natural vitamin A and alkanoyl esters thereof, the five conjugated double-bonds all have the trans-configuration. Of all the isomers, all-trans vitamin A or alkanoyl esters thereof, possess by far the greatest biological activity and are accordingly used almost exclusively in human and animal nutrition. Since present commercial vitamin A preparations are almost exclusively of the synthetic type and since the hitherto known and used processes for the manufacture of vitamin A do not yield pure all-trans compounds, but rather mixtures of various isomers containing more or less large amounts of the all-trans isomer, there has always been the problem of isomerizing the various isomers into the all-trans compound, the isomerization of the 9-cis compound into the all-trans compound never having been satisfactory achieved. The problem which arise are the obtention of the highest possible yields of all-trans compounds and, since the total cis-trans conversion is not possible, the obtention of mixtures from which the all-trans isomer can be isolated in the easiest possible manner. The method most widely heretofore has been isomerization with iodine in the presence of pyridine. This method is not particularly favorable since only 11-cis and 13-cis as well as 11,13-di-cis isomers, but not 9-cis or 9,13-di-cis isomers can be converted into all-trans compounds. Photochemical isomerization using sensitizers is also known. This method is fraught with disadvantages since, after completion of the isomerization, the sensitizer must be removed. Removal of the sensitizers, especially when working on an industrial scale, can result in considerable difficulties. The irradiation of dilute solutions, in concentrations which are usual in photochemistry, in the absence of sensitizers is also unfavorable for the isomerization since dimers are primarily formed.

Accordingly, the problem to be solved consists in finding and isomerization process whereby there can be obtained from pure isomers or mixtures thereof, a mixture which has the highest possible content of all-trans compound and from which the all-trans isomer can then be isolated readily and in the purest form possible.

SUMMARY OF THE INVENTION

The present invention relates to a process for the photochemical isomerization of vitamin A compounds and of their derivatives.

More particularly, the invention is concerned with a process for the isomerization of 9-cis, 11-cis and 9,11-di-cis vitamin A compounds, derivatives thereof or mixtures of these isomers into the corresponding all-trans compounds. An additional aspect of this invention is a process for the isomerization of all-trans and 11-cis vitamin A compounds and derivatives thereof as well as of mixtures of these isomers into the corresponding 9-cis compounds.

The vitamin A compounds and derivatives thereof which are isomerized according to the process of this invention are those having the following formula:

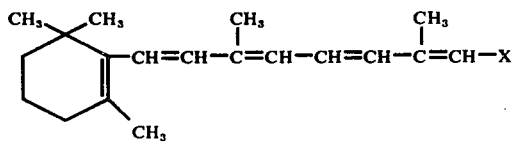

wherein X is selected from the group consisting of —CHO, —CH$_2$OH, —COOH, —CH(R)$_2$, —CH$_2$OR$_1$, —COOR$_2$, —CONHR$_3$ or CON(R$_3$)$_2$ in which R is lower alkoxy or two R's taken together are lower alkylenedioxy; R$_1$ is alkanoyl or aroyl, R$_2$ is an alkyl, aryl or aralkyl group and R$_3$ is hydrogen, alkyl, aryl or aralkyl.

DETAILED DESCRIPTION OF THE INVENTION

As used herein, the term "alkanoyl" means a straight-chain or branched-chain alkanoyl group containing from 1 to 18 carbon atoms, e.g., formyl, acetyl, propionyl, butyryl, stearoyl, palmitoyl and the like. The term "aroyl" means an aroyl group which is preferably derived from an aromatic carboxylic acid containing from 7 to 11 carbon atoms, e.g., benzoyl. The term "alkyl" means a straight-chain or branched-chain alkyl group containing from 1 to 18 carbon atoms, e.g., methyl, ethyl, propyl, butyl, decyl, dodecyl, hexadecyl, octadecyl and the like. The term "aryl" means substituted or unsubstituted phenyl naphthyl, azulyl, phenanthryl. Preferred aryl groups are phenyl or naphthyl. The term "aralkyl" means an aralkyl group containing from 1 to 4 carbon atoms in the aliphatic moiety, e.g., benzyl, phenylpropyl and the like. The term "lower alkoxy" means an alkoxy group containing from 1 to 6 carbon atoms, e.g., methoxy, ethoxy, propoxy and the like. The term "lower alkylenedioxy" means an alkylenedioxy group containing from 1 to 6 carbon atoms, e.g., methylenedioxy, ethylenedioxy and the like.

In accordance with the present invention, the foregoing problem has now been solved by a process which comprises irradiating an all-trans, a 9-cis, an 11-cis or a 9,11-di-cis isomer or a mixture thereof in liquid form or in the form of an at least 3% (wt./vol.) solution, whereby the compound to be isomerized must not be completely dissolved, with light in the wavelength between about 240 and about 450 nanometers (nm(10$^{-9}$, meters, preferably between about 320 and about 400 nm, in the absence of sensitizers.

It has been found in accordance with the present invention that by isomerizing not only pure all-trans, 9-cis, 11-cis or 9,11-di-cis isomers of vitamin A compounds or their derivatives but also any mixtures thereof, there is obtained an isomer mixture which consists of about 40–90% (about 60–90% in the case of vitamin A acetate) of all-trans compound, of about 10–30% of 9-cis compound and of up to about 5% of 13-cis compound and, when an aldehyde of formula I is used, of up to about 20% of 13-cis compound. The respective all-trans compound can be isolated from this mixture without difficulty, i.e., by simple crystallization. It is even possible to obtain the practically pure all-trans compound by a single crystallization from such a mixture which does not contain the 13-cis isomer or which contains only a small amount (up to about 3–5%) thereof.

Since the isomerization of 11-cis compounds to all-trans compounds proceeds much quicker than the isomerization of all-trans compounds to 9-cis compounds, the amount of the latter, in the case where 11-cis compounds or mixtures containing same are isomerized, is smaller than that given earlier in the previously mentioned isomer mixture and may even be less than 10%.

In accordance with the present invention, it is possible to increase the yield of all-trans compound in vitamin A syntheses or the purity of the end product since the 9-cis isomer which is present in relatively large amounts in the reaction mixture can be isomerized to the all-trans compound. Likewise, the present invention enables the use of syntheses which yield mainly the 9-cis isomer. Such syntheses have not been employed heretofore because of the difficulties encountered in converting the 9-cis isomer to the all-trans compound.

An additional advantage of the process of the present invention is that is is now possible to readily manufacture pure 9-cis vitamin A or 9-cis vitamin A acetate which heretofore have only been obtainable by an extremely complicated and expensive procedure. The manufacture of pure 9-cis vitamin A or 9-cis vitamin A acetate can be carried out as follows: pure all-trans or 11-cis vitamin A acetate or a mixture thereof is isomerized in accordance with the invention. There is thus obtained a mixture of all-trans and 9-cis vitamin A acetate as described previously, from which the all-trans isomer can readily be crystallized. The mother liquor remaining has a high content of 9-cis vitamin A acetate which can be converted into the corresponding alcohol and this alcohol can be crystallized. The pure 9-cis vitamin A alcohol can then be re-converted into the acetate if desired. Also if desired, the pure 9-cis vitamin A alcohol can be converted into the corresponding aldehyde or into the corresponding acid.

The process provided by the present invention is preferably carried out using compounds of formula I in which X represents the group —$CH_2OR_1$ (especially where $R_1$ represents the acetyl group) or the group —CHO.

Where mixtures of compounds of formula I are used, these are preferably mixtures which contain 9-cis and all-trans vitamin A acetate and especially mixtures which contain from about 50 to about 70% of 9-cis vitamin A acetate and from about 30 to about 50% of all-trans vitamin A acetate. There are also preferred mixtures of 9-cis, 11-cis and all-trans vitamin A acetate, especially mixtures which contain from about 0 to about 15% of 9-cis, from about 20 to about 40% of 11-cis and from about 40 to about 70% of all-trans vitamin A acetate.

The isomerization is conveniently carried out in an inert organic solvent, especially in such a solvent which does not absorb in the wavelength range of about 240 to about 450 nm. As suitable solvents there may be mentioned polar solvents, especially aprotic solvents such as acetonitrile, dimethylformamide and the like. However, non-polar solvents such as aliphatic and aromatic hydrocarbons, e.g., pentane, hexane, heptane, benzene, toluene, xylene, petroleum ether and the like are preferred. Halogenated aliphatic and aromatic hydrocarbons, e.g., methylene chloride, ethylene chloride, chloroform, carbon tetrachloride, chlorobenzene etc. can also be used. Lower aliphatic alcohols, e.g., methanol, ethanol, propanol etc. can also be used. Solvent mixtures can also be used. An especially preferred solvent is n-hexane.

Insofar as the compound to be isomerized is present in liquid form, the isomerization can also be carried out in the absence of a solvent. The use of solvent is, however, preferred.

When solutions are used in the isomerization, these are, as already mentioned, at least 3% (wt./vol.) solutions since in the case of smaller concentrations, i.e., concentrations which are normally customary in the case of photochemical reactions, a large amount of the material used dimerizes as already mentioned. There are preferably used up to about 400% (wt./vol.), especially from about 15 to about 200% (wt./vol.), solutions. Especially preferred are about 100% (wt./vol.) solutions since these also represent the best conditions for subsequent crystallization of the all-trans isomer.

As already mentioned, the isomerization is carried out by irradiation with light in the wavelength range between about 240 and about 450 nm, preferably between about 320 and about 400 nm. The isomerization can be carried out using any light source which emits light in this wavelength range. In order to avoid irradiation with shorter wavelength light than that previously specified, suitable filters can be used.

The isomerization can be conveniently carried out at a temperature of from about −70° to about 200° C. The isomerization is preferably carried out at a temperature of from about −40° to about 150° C., particularly of from about 0° to about 100° C. It is especially preferred to carry out the isomerization at a temperature between about 10° C and about 70° C. Conveniently, in the case of cis to trans isomerization, the concentration and the temperatures are chosen so that the all-trans isomer formed is separated continuously.

The isomerization may be carried out over a period of from about 1 minute to about 50 hours, preferably between about 10 minutes and about 10 hours and most preferably between about 10 minutes and about 6 hours. Isomerization times of less than one minute and greater than 50 hours may be employed, although, no beneficial results are realized thereby. The isomerization time is largely dependent on the light intensity in that lower intensity and longer isomerization time bring about the same effect as high intensity and correspondingly shorter isomerization time. Since known vitamin A compounds and derivatives thereof are somewhat unstable compounds, the isomerization conditions are expediently selected so that the isomerization mixture is not heated for a long time at high temperatures or is not subjected to great light intensities.

The isomerization is conveniently carried out in the absence of air, that is to say, under an inert gas atmosphere such as nitrogen, argon, etc. Furthermore, the isomerization can be carried out batch-wise or continuously.

The isomerization is conveniently carried out in the presence of a weak organic base. Organic bases which can be used are primary, secondary and, especially, tertiary amines, e.g., propylamine, diethylamine, triethylamine, tripropylamine, 1,4-diazobicyclooctane etc.

The following examples illustrate the present invention. In the examples, complete analyses by liquid chromatography (LC) were carried out.

EXAMPLE 1

31 g. of a mixture containing 60% of 9-cis vitamin A acetate and 40% of all-trans vitamin A acetate are dissolved under argon in 31 ml. of n-hexane and 800 μl of tripropylamine in a round Pyrex flask. This solution is irradiated while stirring at 65° C. for 6 hours with a 150 Watt xenon lamp arranged outside th Pyrex flask. There is obtained a mixture containing 29.7% of 9-cis and 65.3% of all-trans vitamin A acetate. This mixture is diluted with 62 ml. of n-hexane and then cooled down to −40° C., whereby all-trans vitamin A acetate precipitates (17 g. having 98.3% purity).

The concentrated mother liquor is treated with the same amount of n-hexane so that there is obtained a 100% solution (wt./vol.). After irradiation for 4 hours under the same conditions as described above and crystallization, there are obtained an additional 6 g. of all-trans vitamin A acetate (96% purity). The procedure is carried out again a third time with irradiation for 3 hours and there are obtained an additional 3 g. of all-trans vitamin A acetate (95% purity). The total yield amounts to 84%.

EXAMPLE 2

A vitamin A derivative is dissolved in n-hexane in the presence of tripropylamine in a round Pyrex flask with the formation of a 100% (wt./vol.) solution. The Pyrex flask is flushed through the argon and closed. The solution is then irradiated with a 150 Watt xenon lamp at constant temperature and while stirring. The results obtained are given in the following table:

VAAc : Vitamin A acetate
VAAlc : Vitamin A alcohol
VAAld : Vitamin A aldehyde
VAPalm : Vitamin A palmitate
TPA : Tripropylamine.

We claim:
1. The process for the photochemical isomerization of a compound of the formula:

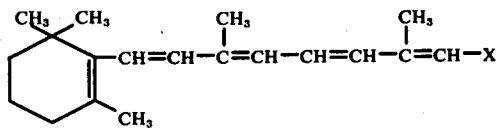

wherein X is selected from the group consisting of —CHO, —CH$_2$OH, —COOH, CH(R)$_2$, —CH$_2$OR$_1$, —COOR$_2$, —CONHR$_3$ or —CON(R$_3$)$_2$ in which R is lower alkoxy or two R's taken together are lower alkylenedioxy, R$_1$ is alkanoyl or aroyl, R$_2$ is an alkyl, aryl or aralkyl group and R$_3$ is hydrogen, alkyl, aryl or aralkyl;
which process comprises irradiating a 9-cis isomer, an 11-cis isomer, a 9,11-di-cis isomer or mixtures thereof in either liquid form or in the form of at least 3% (wt./vol.) solutions with light having a wavelength range of about 240 nm to about 450 nm in the absence of sensitizers.

2. A process according to claim 1 wherein X is —CH-

Table 1

| Starting material | Solvent | Base | Isomerization duration in minutes | Isomerization temperature °C. | 9-cis compound % | all-trans compound % | 13-cis compound % | 11-cis compound % |
|---|---|---|---|---|---|---|---|---|
| 5 g all-trans VAAc | 5 ml n-hexane | 100 μl TPA | 60 | 65 | 20.7 | 71.6 | 0.8 | |
| 2 g 9-cis VAAc | 2 ml n-hexane | 40 μl TPA | 120 | 65 | 26.7 | 69.5 | 0.5 | |
| 0.9 g 11-cis VAAc | 0.9 ml n-hexane | 10 μl TPA | 30 | 65 | 21.1 | 76.0 | <1.0 | 1.0 |
| 2.6 g mixture of 65% all trans and 35% 11-cis VAAc | 2.6 ml n-hexane | 20 μl TPA | 20 | 65 | 15.4 | 75.3 | 0.1 | 4.8 |
| | | | 30 | 65 | 19.5 | 75.6 | 0.4 | 1.6 |
| 2 g all-trans VAAlC | 2 ml n-hexane | 25 μl TPA | 15 | 65 | 10.2 | 88.8 | | |
| | | | 30 | 65 | 17.0 | 81.3 | | |
| | | | 45 | 65 | 20.3 | 78.5 | | |
| 5 g all-trans VAAld | 5 ml n-hexane | 500 μl TPA | 45 | 65 | 11.7 | 81.0 | 4.6 | |
| | | | 120 | 65 | 15.5 | 76.7 | 9.9 | |
| 5 g all-trans VAPalm | 5 ml n-hexane | 100 μl TPA | 60 | 65 | 13.4* | 82.9* | 3.7* | |
| | | | 120 | 65 | 28.8 | 67.6 | 3.7 | |
| 1 g all-trans Vitamin A acid methyl ester | 1 ml n-hexane | 10 μl TPA | 30 | 65 | 10.7* | 86.6* | 2.7* | |
| | | | 45 | 65 | 15.7 | 80.2 | 4.1 | |
| | | | 60 | 65 | 19.7 | 75.1 | 5.3 | |

*there are area percents

EXAMPLE 3

20 g. of all-trans vitamin A acetate are dissolved in 20 ml. of solvent in the presence of 400 μl of tripropylamine in an isomerization vessel having a built-in 150 Watt Hg high-pressure lamp. The vessel consisting of Duran glass is enveloped with aluminum foil during the irradiation. The results obtained are compiled in the following Table:

$_2$OR$_1$.

3. A process according to claim 2 wherein R$_1$ is acetyl.
4. A process according to claim 1 wherein X is —CHO.
5. A process according to claim 1 wherein the isomerization is carried out in a non-polar solvent.
6. A process according to claim 1 wherein the isomerization is carried out continuously.

* * * * *

Table 2

| Isomerization time in minutes | Isomerization temperature °C. | Solvent | 13-cis compound % | 9-cis compound % | all-trans compound % |
|---|---|---|---|---|---|
| 8 | 65 | n-hexane | 2.6 | 18.7 | 75.2 |
| 8 | 32 | n-pentane* | 1.9 | 14.1 | 82.9 |
| 8 | 65 | ethanol | 3.2 | 11.0 | 73.5 |
| 8 | 65 | isopropanol | 1.8 | 10.0 | 76.5 |
| 8 | 25 | chloroform | 3.0 | 9.5 | 75.0 |
| 8 | 26 | ether | 1.6 | 10.9 | 75.6 |
| 8 | 25 | acetone | 3.1 | 10.7 | 76.9 |
| 8.5 | 65 | acetonitrile | 3.5 | 15.7 | 73.4 |

*Here the isomer was only partially dissolved.